(12) United States Patent
Henderson et al.

(10) Patent No.: US 10,384,007 B2
(45) Date of Patent: Aug. 20, 2019

(54) AUTO-INJECTOR

(71) Applicant: SANOFI-AVENTIS DEUTSCHLAND GMBH, Frankfurt am Main (DE)

(72) Inventors: Charley Henderson, Cambridgeshire (GB); David Cross, Hertfordshire (GB); Douglas Ivan Jennings, Hertfordshire (GB); Ryan Anthony McGinley, Cambridgeshire (GB)

(73) Assignee: Sanofi-Aventis Deutschland GMBH, Frankfurt am Main (DE)

( * ) Notice: Subject to any disclaimer, the term of this patent is extended or adjusted under 35 U.S.C. 154(b) by 292 days.

(21) Appl. No.: 14/435,563

(22) PCT Filed: Oct. 2, 2013

(86) PCT No.: PCT/EP2013/070584
§ 371 (c)(1),
(2) Date: Apr. 14, 2015

(87) PCT Pub. No.: WO2014/060216
PCT Pub. Date: Apr. 24, 2014

(65) Prior Publication Data
US 2016/0175524 A1    Jun. 23, 2016

(30) Foreign Application Priority Data
Oct. 18, 2012   (EP) .................................... 12189092

(51) Int. Cl.
*A61M 5/20* (2006.01)
*A61M 5/32* (2006.01)
*A61M 5/315* (2006.01)

(52) U.S. Cl.
CPC ...... *A61M 5/2033* (2013.01); *A61M 5/31543* (2013.01); *A61M 5/3204* (2013.01);
(Continued)

(58) Field of Classification Search
CPC ............ A61M 5/3157; A61M 5/31543; A61M 2005/202; A61M 2005/206; A61M 2005/2073; A61M 5/3137; A61M 5/31526
See application file for complete search history.

(56) References Cited

U.S. PATENT DOCUMENTS 5,042,977 A * 8/1991 Bechtold ................. A61M 5/20
                                                    604/134
6,203,529 B1 * 3/2001 Gabriel ............... A61M 5/3202
                                                    604/192
(Continued)

FOREIGN PATENT DOCUMENTS

CN    101479000    7/2009
CN    101801441    8/2010
(Continued)

OTHER PUBLICATIONS

Extended European Search Report in Application No. 12189092.5, dated Mar. 6, 2013, 5 pages.
(Continued)

*Primary Examiner* — Jason E Flick
*Assistant Examiner* — Courtney B Fredrickson
(74) *Attorney, Agent, or Firm* — Fish & Richardson P.C.

(57) ABSTRACT

Described is an auto-injector for administering a medicament comprising a case arranged to receive a packaged syringe comprising an injection needle, wherein the case comprises a front case rotatably coupled to a rear case, and a drive spring arranged to advance a plunger relative to the packaged syringe, and a reset mechanism for the drive spring arranged to retract the plunger and compress the drive spring when the front case is rotated relative to the rear case.

15 Claims, 11 Drawing Sheets

Specification includes a Sequence Listing.

(52) U.S. Cl.
CPC ..... *A61M 5/3157* (2013.01); *A61M 2005/202* (2013.01); *A61M 2005/206* (2013.01); *A61M 2005/2013* (2013.01); *A61M 2005/2073* (2013.01); *A61M 2005/31588* (2013.01); *A61M 2205/3553* (2013.01); *A61M 2205/52* (2013.01); *A61M 2205/581* (2013.01); *A61M 2205/6045* (2013.01); *F04C 2270/0421* (2013.01)

(56) References Cited

U.S. PATENT DOCUMENTS

| | | | | |
|---|---|---|---|---|
| 2002/0120235 | A1* | 8/2002 | Enggaard | A61M 5/20 604/135 |
| 2002/0165500 | A1* | 11/2002 | Bechtold | A61M 5/2033 604/209 |
| 2006/0229570 | A1* | 10/2006 | Lovell | A61M 5/20 604/218 |
| 2007/0021720 | A1* | 1/2007 | Guillermo | A61M 5/2033 604/187 |
| 2010/0152671 | A1* | 6/2010 | Raab | A61M 5/31551 604/207 |
| 2011/0034881 | A1* | 2/2011 | Bartha | A61M 5/24 604/211 |
| 2011/0092905 | A1 | 4/2011 | Cowe | |
| 2012/0136315 | A1* | 5/2012 | Wieselblad | A61M 5/20 604/189 |
| 2012/0184917 | A1* | 7/2012 | Bom | A61M 5/24 604/187 |
| 2013/0035642 | A1* | 2/2013 | Daniel | A61M 5/2033 604/189 |
| 2014/0243757 | A1* | 8/2014 | Dasbach | A61M 5/20 604/221 |

FOREIGN PATENT DOCUMENTS

| | | | |
|---|---|---|---|
| CN | 102596291 | 7/2012 | |
| EP | 2 468 329 | 6/2012 | |
| GB | 2 452 286 | 3/2009 | |
| JP | 2004/516895 | 6/2004 | |
| JP | 2005/261855 | 9/2005 | |
| WO | WO 02/053214 | 7/2002 | |
| WO | WO 2009/097934 | 8/2009 | |
| WO | WO 2010142598 A2 * | 12/2010 | ............. A61M 5/20 |
| WO | WO 2011/101382 | 8/2011 | |
| WO | WO 2011/123024 | 10/2011 | |
| WO | WO 2012085028 A1 * | 6/2012 | ......... A61M 5/2033 |
| WO | WO 2012/130901 | 10/2012 | |

OTHER PUBLICATIONS

International Preliminary Report on Patentability in International Application No. PCT/EP2013/070584, dated Apr. 21, 2015, 6 pages.
International Search Report and Written Opinion in International Application No. PCT/EP2013/070584, dated Dec. 11, 2013, 9 pages.
Chinese Office Action in Application No. 2013/80065504.5, dated Sep. 11, 2017, 8 pages.

* cited by examiner

SEQUENCE LISTING

```
<160> NUMBER OF SEQ ID NOS: 1

<210> SEQ ID NO 1
<211> LENGTH: 39
<212> TYPE: PRT
<213> ORGANISM: Artificial Sequence
<220> FEATURE:
<223> OTHER INFORMATION: Exendin-4

<400> SEQUENCE: 1

His Gly Glu Gly Thr Phe Thr Ser Asp Leu Ser Lys Gln Met Glu Glu
1               5                   10                  15

Glu Ala Val Arg Leu Phe Ile Glu Trp Leu Lys Asn Gly Gly Pro Ser
            20                  25                  30

Ser Gly Ala Pro Pro Pro Ser
        35
```

AUTO-INJECTOR

This application is a 371 U.S. National Application of PCT/EP2013/070584, filed on Oct. 2, 2013, which claims priority to European Patent Application Nos. 12189092.5, filed on Oct. 18, 2012, the entire contents of which are incorporated herein by reference.

TECHNICAL FIELD

The invention relates to an auto-injector for administering a medicament.

BACKGROUND OF THE INVENTION

Administering an injection is a process which presents a number of risks and challenges for users and healthcare professionals, both mental and physical Injection devices typically fall into two categories—manual devices and auto-injectors. In a conventional manual device, a user must provide force to drive a medicament through a needle. This is typically done by some form of button/plunger that has to be continuously pressed during the injection. There are numerous disadvantages for the user from this approach. For example, if the user stops pressing the button/plunger, the injection will stop and may not deliver an intended dose to a patient. Further, the force required to push the button/plunger may be too high for the user (e.g., if the user is elderly). And, aligning the injection device, administering the injection and keeping the injection device still during the injection may require dexterity which some patients (e.g., elderly patients, children, arthritic patients, etc.) may not have.

Autoinjector devices aim to make self-injection easier for patients. A conventional autoinjector may provide the force for administering the injection by a spring, and trigger button or other mechanism may be used to activate the injection. Autoinjectors may be single-use or reusable devices.

An electro-mechanical re-usable auto-injector may comprise an electromechanical re-usable device into which a syringe or cartridge can be loaded by the user. The electro-mechanical re-usable device may be used to perform multiple parenteral drug deliveries, whereas the syringe or cartridge is disposable. The syringe or cartridge may be packaged with additional parts to provide additional functionality.

There remains a need for an improved auto-injector.

SUMMARY OF THE INVENTION

It is an object of the present invention to provide an improved auto-injector.

In an exemplary embodiment, an auto-injector according to the present invention comprises a case arranged to receive a packaged syringe comprising an injection needle. The case comprises a front case rotatably coupled to a rear case. The auto-injector further comprises a drive spring arranged to advance a plunger relative to the syringe, and a reset mechanism for the drive spring arranged to retract the plunger and compress the drive spring when the rear case is rotated relative to the front case.

In an exemplary embodiment the plunger comprises a threaded extension and wherein a screw nut is arranged in the rear case in a manner releasably engaging the threaded extension such that the plunger is retractable by rotation of the rear case relative to the front case.

In an exemplary embodiment the screw nut is arranged as a ratchet wheel coupled to at least one ratchet drive feature in the rear case thus coupling the ratchet wheel to the rear case in one sense of rotation and allowing rotation of the ratchet wheel within the rear case in an opposite sense of rotation.

In an exemplary embodiment at least one release clip is arranged in the screw nut and biased to engage the threaded extension.

In an exemplary embodiment the release clip is arranged to release the threaded extension when a trigger sleeve is translated in a proximal direction relative to the case.

In an exemplary embodiment the rear case and front case comprise respective thumb rests with direction symbols indicating the sense of rotation for resetting the drive spring.

In an exemplary embodiment an electric motor powered by a battery is arranged for retracting the plunger.

In an exemplary embodiment a gear train is arranged to convert rotation of the electric motor into linear motion of the plunger, wherein the gear train comprises a rack (16.6) and a pinion gear.

In an exemplary embodiment the gear train comprises a clutch coupling the motor to the plunger for retracting the plunger in a proximal direction and decoupling the plunger from the motor when the plunger is moved in a distal direction.

In an exemplary embodiment the auto-injector further comprises a syringe carrier for retaining the syringe and a control spring arranged to advance the syringe carrier for needle insertion.

In an exemplary embodiment the plunger is coupled to the syringe carrier when at least nearly fully retracted and released from the syringe carrier when the syringe carrier is advanced to a predetermined position relative to the case.

In an exemplary embodiment the control spring distally bears against a control collar operatively coupled to the syringe carrier or the trigger sleeve depending at least on a position of the trigger sleeve relative to the case.

In an exemplary embodiment a releasable noise rod is provided, capable of, upon release, generating an audible and/or tactile feedback to a user, wherein the noise rod is arranged to be released when the plunger reaches a position relative to the syringe in which a stopper is located in proximity of a distal end of the syringe.

In an exemplary embodiment the packaged syringe comprises a syringe case, wherein a protective cap is arrangeable on the syringe case, the cap having an inner sleeve arrangeable inside the trigger sleeve and over a protective needle boot for protecting the needle, wherein a barb is attached in the inner sleeve engageable to the protective needle boot for joint axial translation.

In an exemplary embodiment a control unit is arranged for storing time stamped user operations and for exchanging data with an external data base.

The auto-injector provides a means for the patient to inject themselves with drugs, with a minimum requirement of technical training or dexterity thus removing the need for a trained clinician to be present.

The auto injector may typically be arranged to replaceably receive a pre-filled syringe or cartridge. The work that would previously be performed by a clinician is then divided between the patient and the auto-injector. Typically, the patient locates the auto-injector on their skin to start the injection process. The auto-injector then inserts a needle into the patient's skin, depresses a plunger to dispense the drug, and then removes the needle such that the resulting assembly is needle safe.

A re-usable mechanical auto-injector with mechanical or electromechanical reset may comprise a mechanical re-usable device into which a pre-filled syringe or cartridge can be loaded by the user, spring actuated needle insertion and drug dispense, and a mechanical or electromechanical, e.g. motor driven mechanism that resets the spring.

The auto-injector according to the invention is particularly simple and compact. A re-usable device with a disposable packaged syringe allows for reducing the amount of waste and has thus a low environmental impact.

Further scope of applicability of the present invention will become apparent from the detailed description given hereinafter. However, it should be understood that the detailed description and specific examples, while indicating preferred embodiments of the invention, are given by way of illustration only, since various changes and modifications within the spirit and scope of the invention will become apparent to those skilled in the art from this detailed description.

BRIEF DESCRIPTION OF THE DRAWINGS

The present invention will become more fully understood from the detailed description given hereinbelow and the accompanying drawings which are given by way of illustration only, and thus, are not limitive of the present invention, and wherein.

DETAILED DESCRIPTION

Figure 1:
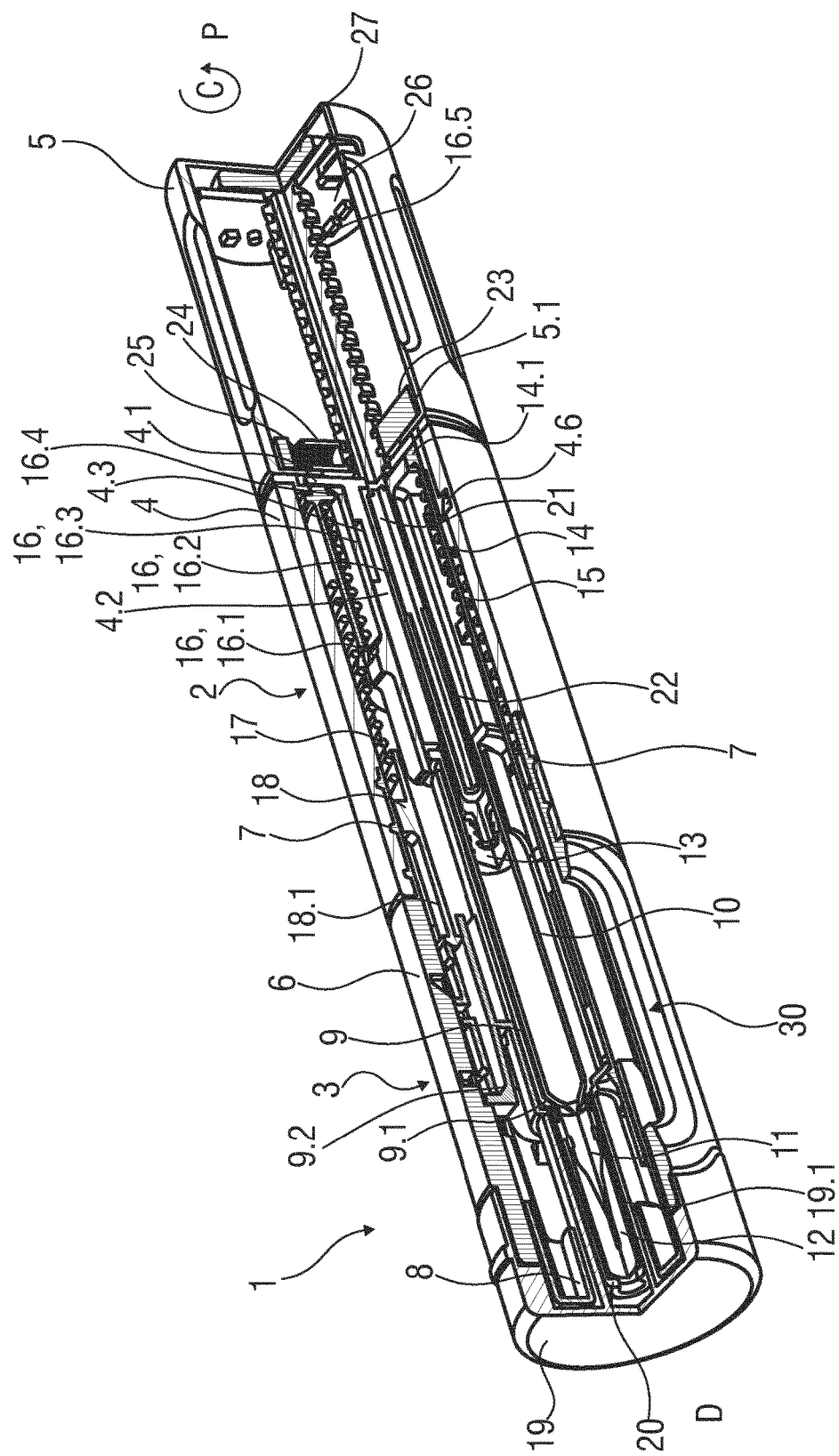
FIG. 1 is a perspective sectional view of the auto-injector prior to use.

FIG. 1 is a perspective sectional view of an exemplary embodiment of an auto-injector 1. The auto-injector 1 comprises a re-usable device 2 and a disposable packaged syringe 3. The reusable device 2 comprises an essentially cylindrical front case 4 and an essentially cylindrical rear case 5.

The packaged syringe 3 comprises an essentially cylindrical syringe case 6. The syringe case 6 and the front case 4 are adapted to be connected by a screw connection 7. In alternative embodiments the syringe case 6 and the front case 4 could likewise be connected differently, e.g. by a bayonet fit, snap-fit etc.

The packaged syringe 3 comprises a trigger sleeve 8 telescoped within the syringe case 6. An essentially tubular front syringe carrier 9 is telescoped within the trigger sleeve 8.

A syringe 10, e.g. a standard 1 ml syringe or a Hypak syringe, with a hollow injection needle 11 is arranged within the syringe carrier 9. The syringe 10 is locked in an axial direction with respect to the syringe carrier 9. For this purpose the syringe carrier 9 incorporates a collar 9.1 for supporting the syringe 10 at its distal end. When the packaged syringe 3 is assembled a protective needle boot 12 is attached to the needle 11. A stopper 13 is arranged for sealing the syringe 10 proximally and for displacing a liquid medicament M through the needle 11.

In an exemplary embodiment an electronic skin contact sensor may be arranged in addition to the trigger sleeve 8. The skin contact sensor may provide additional functionality and communicate with a control unit 26 in the auto-injector 1 to give an indication of correct skin contact.

The front syringe carrier 9 is locked to the syringe case 6 by a resilient beam 9.2 abutting a stop in the syringe case 6.

In the state as delivered as shown in FIG. 1 a protective cap 19 is attached to the distal end of the syringe case 6 and the protective needle boot 12 is in place over the needle 11 and the needle hub. An inner sleeve 19.1 of the cap 19 is arranged inside the trigger sleeve 8 and over the protective needle boot 12. In the inner sleeve 19.1 a barb 20 is attached. The barb 20 is engaged to the protective needle boot 12 for joint axial translation. The cap 19 protects an aperture in the trigger sleeve 8 against ingress of dirt and shrouds the trigger sleeve 8 to protect the user against unintentional activation and needle stick injury. The protective needle boot 12 may be arranged as a rigid needle shield or a rubber needle shield.

The mechanical features of the packaged syringe 3 allow for differentiating the packaged syringe 3 from a standard syringe and prevent the re-usable device 2 from being used with the wrong type of syringe thus ensuring that the intended drug is used with the auto-injector 1.

A rear syringe carrier 14 is telescoped within the front case 4 of the reusable device 2. A drive spring 15 in the shape of a compression spring is arranged in the rear syringe carrier 14. A plunger 16 serves for forwarding the force from the drive spring 15 to the stopper 13. The plunger 16 is keyed to the front case 4 so as to prevent relative rotation but to allow relative axial translation.

The drive spring 15 is loaded between a proximal end collar 14.1 of the rear syringe carrier 14 and a thrust face 16.1 arranged on the plunger 16.

The front case 4 comprises a proximal end face 4.1 from which a plunger guiding casework 4.2 extends in the distal direction D. An inner piston rod 16.2 of the plunger 16 is telescoped within the plunger guiding casework 4.2. A number of resilient plunger arms 16.3 extend outwardly of the plunger guiding casework 4.2. The thrust face 16.1 is arranged on the plunger arms 16.3. Proximal clips 16.4 on each plunger arm 16.3 are initially arranged proximally behind the proximal end collar 14.1 of the rear syringe carrier 14. The proximal clips 16.4 and the proximal end collar 14.1 are in a ramped engagement so that they may be disengaged by the force of the drive spring 15. However, in the initial state shown in FIG. 1 the plunger arms 16.3 are prevented from flexing inwardly towards each other by the plunger guiding casework 4.2. The engagement of the plunger arms 16.3 behind the proximal end collar 14.1 prevents axial translation of the plunger 16 relative to the rear syringe carrier 14.

A control spring 17 in the shape of another compression spring is arranged over the rear syringe carrier 14 and initially acts between a stop in the front case 4 and a distal control collar 18. In the illustrated embodiment the stop in the front case 4 is provided by a clip 4.6. A resilient member in the shape of an arrowhead 18.1 is distally arranged on the control collar 18. The control collar 18 with the arrowhead 18.1 is being forced in the distal direction D under load of the compressed control spring 17. An outward ramp on the arrowhead 18.1 abuts the trigger sleeve 8 ramping the arrowhead 18.1 inwardly which is prevented by the arrowhead 18.1 inwardly abutting the carrier front syringe carrier 9. Hence, the control collar 18 cannot translate in the proximal direction D. Instead the control collar 18 couples the control spring 17 to the trigger sleeve 8 thereby biasing the trigger sleeve 8 in the distal direction D towards an extended position as illustrated in FIG. 1.

A noise rod 21 is telescoped within a hollow section of the piston rod 16.2. A noise spring 22 is arranged to bias the noise rod 21 in the proximal direction P relative to the piston rod 16.2.

Figure 11:
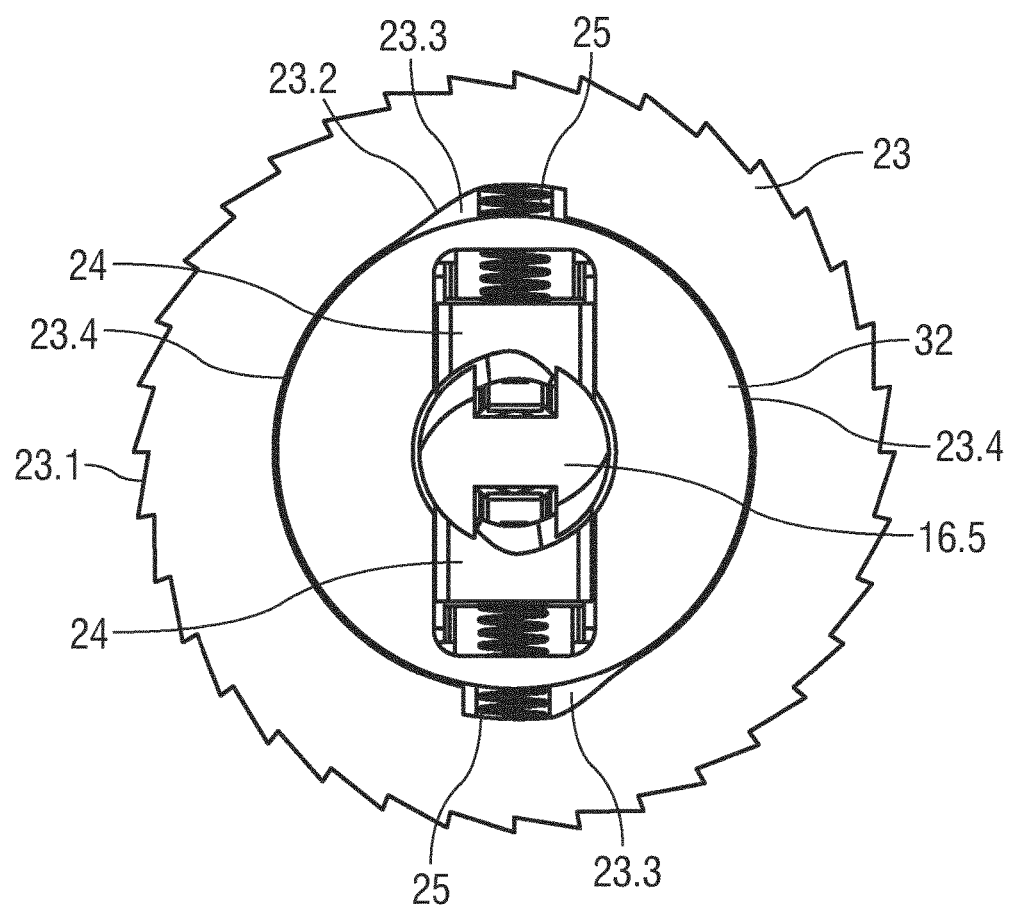
FIG. 11 is a cross sectional view of an embodiment of a ratchet mechanism. Corresponding parts are marked with the same reference symbols in all figures.

The rear case 5 is rotatably arranged with respect to the front case 4. A threaded extension 16.5 on the piston rod 16.2 extends through the proximal end face 4.1 into the rear case 5. A ratchet wheel 23 is arranged around the threaded extension 16.5 within the rear case 5. The ratchet wheel 23 comprises two spring-loaded release clips 24 for releasably engaging the ratchet wheel 23 to the threaded extension 16.5, wherein a respective clip spring 25 biases the release clip 24 into an engaged position as illustrated in FIG. 1. The ratchet wheel 23 exhibits a circumferential toothing 23.1 (cf. FIG. 11) engaged to a number of ratchet drive features 5.1 in the rear case 5. When the rear case 5 is rotated with respect to the front case 4 in a clockwise sense of rotation C the ratchet drive features 5.1 engage the toothing 23.1 of the ratchet wheel 23 so that the ratchet wheel 23 rotates with the rear case 5. The release clips 24 engaged to the threaded extension 16.5 of the piston rod 16.2 pull the piston rod 16.2 and the whole plunger 16 in the proximal direction P thereby resetting the drive spring 15. The ratchet drive features 5.1 allow the user to change the sense of rotation without allowing the plunger 16 to return in the distal direction D as on counterclockwise rotation the ratchet drive features 5.1 are just outwardly deflected by the ratchet toothing 23.1 and jump over the teeth without engaging them. Hence the user may reset the drive spring 15 by a series of reversing rotations about a relatively small angle instead of a number of full rotations which is less convenient. Nevertheless, in an alternative embodiment the rear case 5 may be arranged to releasably engage the threaded extension 16.5 without a ratchet mechanism so that the rear case 5 would have to be fully rotated for resetting the drive spring 15.

Furthermore, the control unit 26 on a printed circuit board and a battery 27 are arranged in the rear case 5. The control unit 26 may be used for compliance monitoring, e.g. by storing time stamped user operations. The auto-injector 1 may be automatically prevented from operating if authentication of the user fails, on an attempt to start an injection at an incorrect time, thus providing patient compliance. Likewise, the control unit 26 may communicate with sensors for detecting skin contact, syringe presence and/or correct assembly of the auto-injector 1. The control unit 26 may be adapted to prevent operation of the auto-injector 1 when it is not in contact with the skin. Communication between the control unit 26 and an external database may be wired or wireless.

A viewing window 30 is arranged in the syringe case 6 for allowing inspection of the syringe 10 and its contents.

An exemplary sequence of operation of the auto-injector 1 is as follows:

The user may retrieve a pre-filled packaged syringe 3 from the fridge and engage it to the re-usable device 2.

Figure 2:
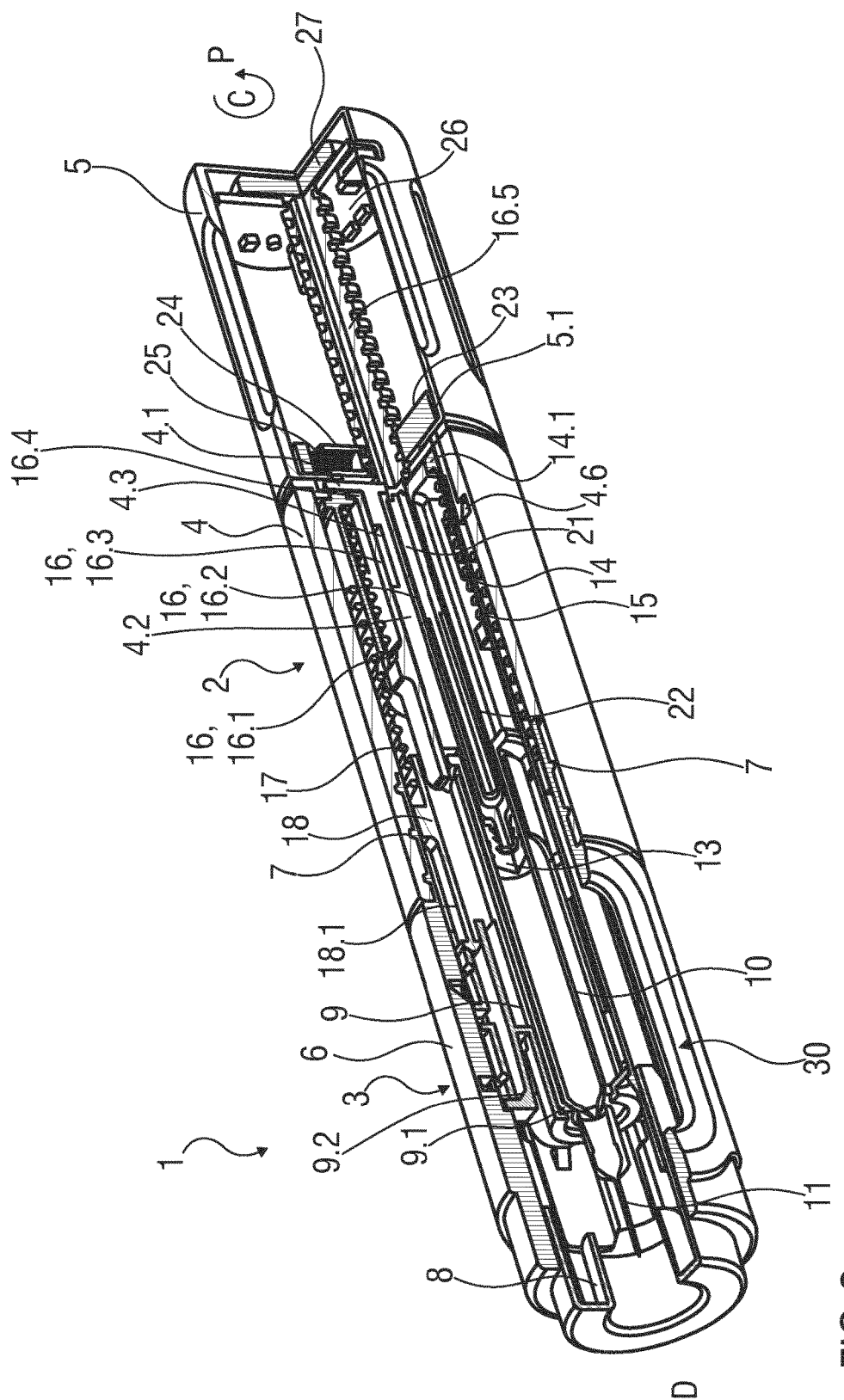
FIG. 2 is a perspective sectional view of the auto-injector after removal of a protective cap.

FIG. 1 is a perspective sectional view of the auto-injector 1 prior to use. The packaged syringe 3 is screwed into the front case 4 of the re-usable device 2. The drive spring 15 is reset. When assembling the packaged syringe 3 and the re-usable device 2 the front syringe carrier 9 and the rear syringe carrier 14 are connected together, e.g. by screw connection, snap fit, bayonet fit, interference fit or any other appropriate means. The user may pull the protective cap 19 from the distal end of the syringe case 6. The barb 20 joins the protective needle boot 12 to the cap 19. Hence, the protective needle boot 12 is also removed on removal of the cap 19. As the beam 9.2 on the front syringe carrier 9 abuts the syringe case 6 the front syringe carrier 9, the syringe 10 and the needle 11 remain in position during boot removal so that the needle 11 is not exposed. FIG. 2 shows the auto-injector 1 with the cap 19 and needle boot 12 removed.

The user may find a preferable injection site and apply an anti-septic swab to clean it.

Figure 3:
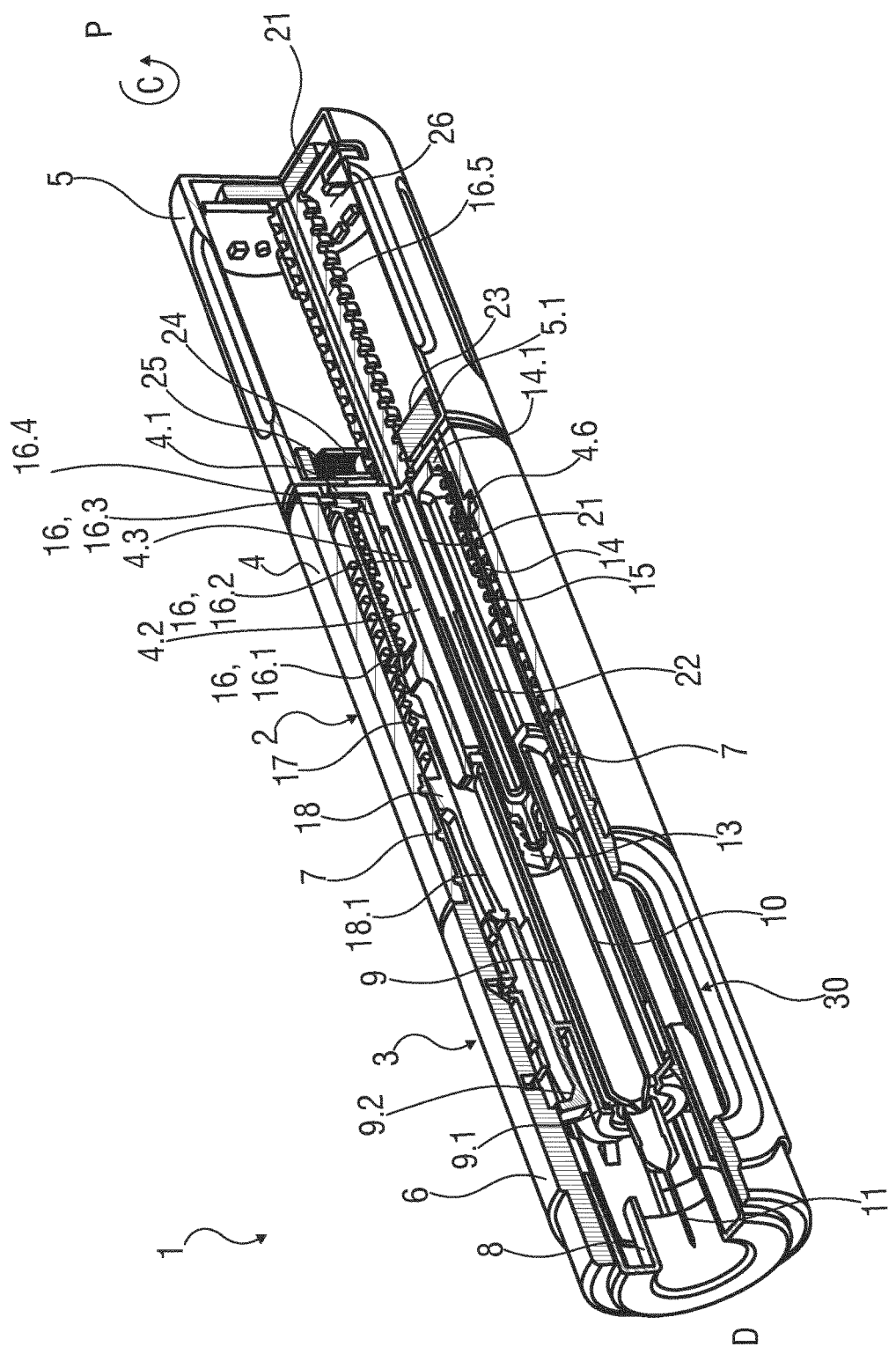
FIG. 3 is a perspective sectional view of the auto-injector with a depressed trigger sleeve.

The user grabs the auto-injector 1 and places the trigger sleeve 8 protruding from the syringe case 6 at the distal end D against an injection site, e.g. a patient's skin. As the auto-injector 1 is pressed against the injection site the trigger sleeve 8 translates in the proximal direction P relative to the syringe case 6 into a retracted position as illustrated in FIG. 3. The control collar 18 is coupled to the trigger sleeve 8 and is thus also moved in the proximal direction P thus slightly compressing the control spring 17. As the trigger sleeve 8 is depressed, the beam 9.2 is deflected by a ramp (not illustrated) on sleeve 8, e.g. disposed a little circumferentially away from the section shown in the figures, allowing the lugs on the ends of beams 9.2 to disengage the syringe case 6 and enter slots in the trigger sleeve 8 so that the front syringe carrier 9 is no longer prevented from being moved in the distal direction D.

If the user was to move the auto-injector 1 away from the injection site prior to reaching the position shown in FIG. 3, the control spring 17 would expand returning the auto-injector 1 to the initial condition after removal of the cap 19 as illustrated in FIG. 2.

Once the trigger sleeve 8 and the control collar 18 reach the position shown in FIG. 3 the arrowhead 18.1 on the control collar 18 is no longer inwardly supported by the front syringe carrier 9. The arrowhead 18.1 is now inwardly deflected under load of the control spring 17 thus decoupling the control collar 18 from the trigger sleeve 8. Instead, the arrowhead 18.1 couples the control collar 18 to the front syringe carrier. Hence, the control spring 17 moves the front syringe carrier 9 in the distal direction D.

Figure 4:
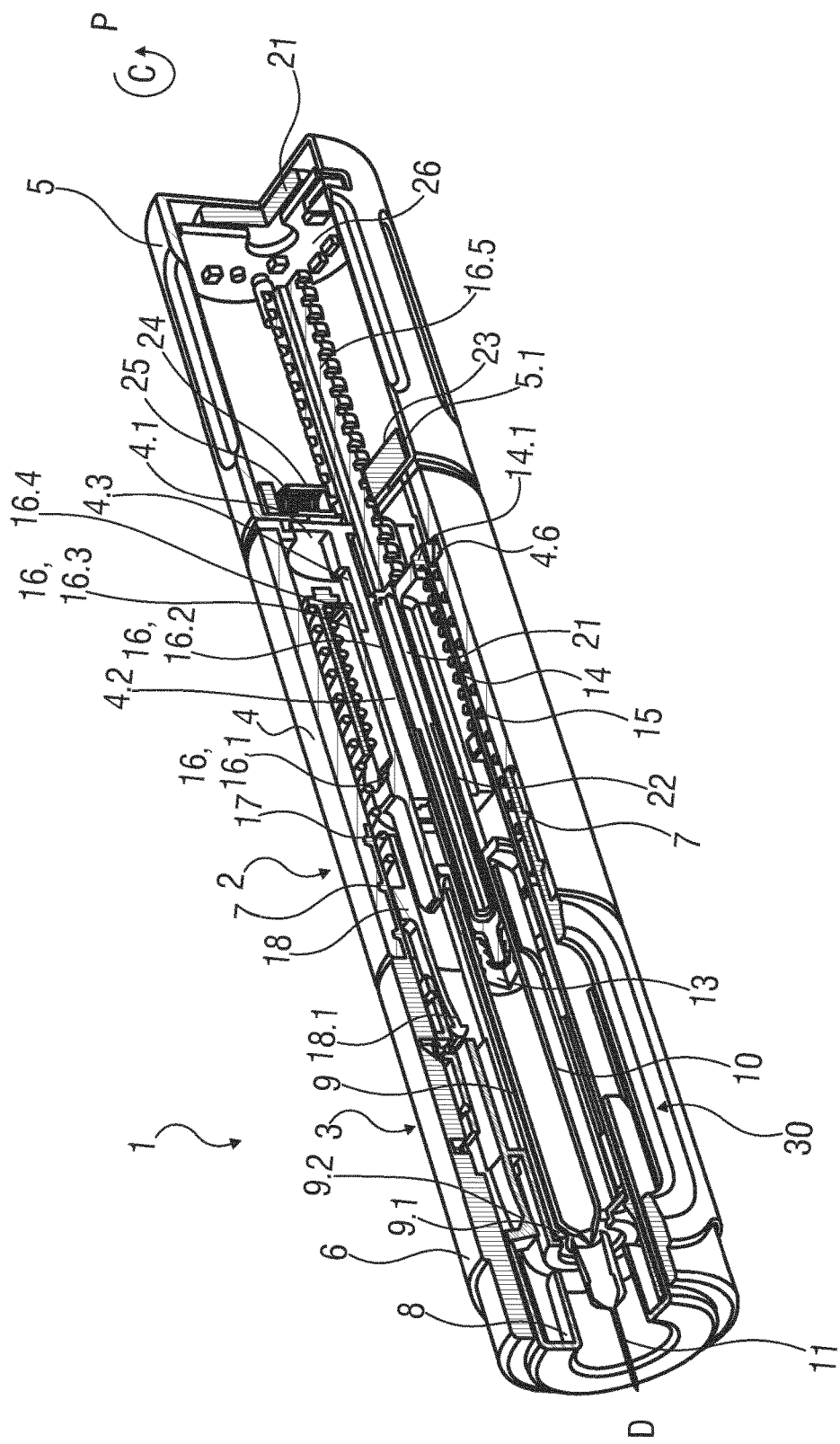
FIG. 4 is a perspective sectional view of the auto-injector with an extended injection needle.

As the whole internal assembly comprising the front syringe carrier 9, the rear syringe carrier 14, the syringe 10, the needle 11 and the plunger 16 are coupled for joint axial translation they are moved as a whole relative to the syringe case 6, front case 4 and rear case by the control spring 17 resulting in the needle 11 protruding from the distal end and being inserted into the injection site as illustrated in FIG. 4. The needle insertion depth is defined by the beam 9.2 on the front syringe carrier 9 abutting the trigger sleeve 8 and by the proximal end collar 14.1 on the rear syringe carrier 14 abutting the proximal end of the control spring 17. As the plunger 16 advances the release clips 24 of the ratchet mechanism jumps over the threads of the threaded extension

16.5. This may be enabled by a portion of the trigger sleeve 8 extending through to the ratchet mechanism, blocking movement of the release clips 24 when the trigger sleeve 8 is extended and or releasing the release clips 24 when the trigger sleeve 8 is depressed. Alternatively, the ratchet mechanism could be adapted to vary the amount of pre-load on the release clips 24 using the mechanism illustrated in FIG. 11. In this modified ratchet mechanism an inner wheel 32 is rotatably arranged within the ratchet wheel 23. The clip springs 25 extend through the inner wheel 32 for engaging an internal surface 23.2 of the ratchet wheel 23 to the release clips 24. The internal surface 23.2 comprises two circular sections 23.4 with a substantially circular cross-section corresponding to an external diameter of the inner wheel 32. Two clearances 23.3 in the internal surface 23.2 locally increase the internal diameter of the ratchet wheel 23. The clearances 23.3 smoothly change over to the circular sections 23.4 of the internal surface 23.2 in one rotational direction thus allowing relative rotation of the inner wheel 32 within the ratchet wheel 23. When the clip springs 25 extend into the clearances 23.3 as in FIG. 11 the pre-load on the release clips 24 is relatively low. When the user twists the rear case 5, the ratchet wheel 23 rotates relative to the inner wheel 32 such that clip springs 25 move into the circular sections 23.4 and become more compressed so that the pre-load is increased. Once reset, the pre-load is removed or reduced by partially counter rotating the rear case 5. The ratchet drive features 5.1 on the rear case 5 may be arranged sufficiently stiff to resolve this load.

As the plunger 16 advances the plunger arms 16.3 with the proximal clips 16.4 move until the clips 16.4 are no longer inwardly supported by the plunger guiding casework 4.2. Instead, a respective recess 4.3 in the plunger guiding casework 4.2 allows inward deflection of the proximal clips 16.4 due to the ramped engagement of the proximal clips 16.4 to the proximal end collar 14.1 and the load from the drive spring 15. Hence, the plunger 16 is released from the rear syringe carrier 14 and driven in the distal direction D by the drive spring 15, ready to push on the stopper 13 and inject the medicament M. Due to the use of separate springs 15, 17 for moving the syringe 10 and the stopper 13 the auto-injector 1 inherently avoids a so called wet injection with drug leaking out of the needle 11 during needle insertion.

While the plunger 16 moves the stopper 13 the movement of the carriers 9, 14 in the distal direction D is completed by the control spring 17 pushing the control collar 18.

Figure 5:
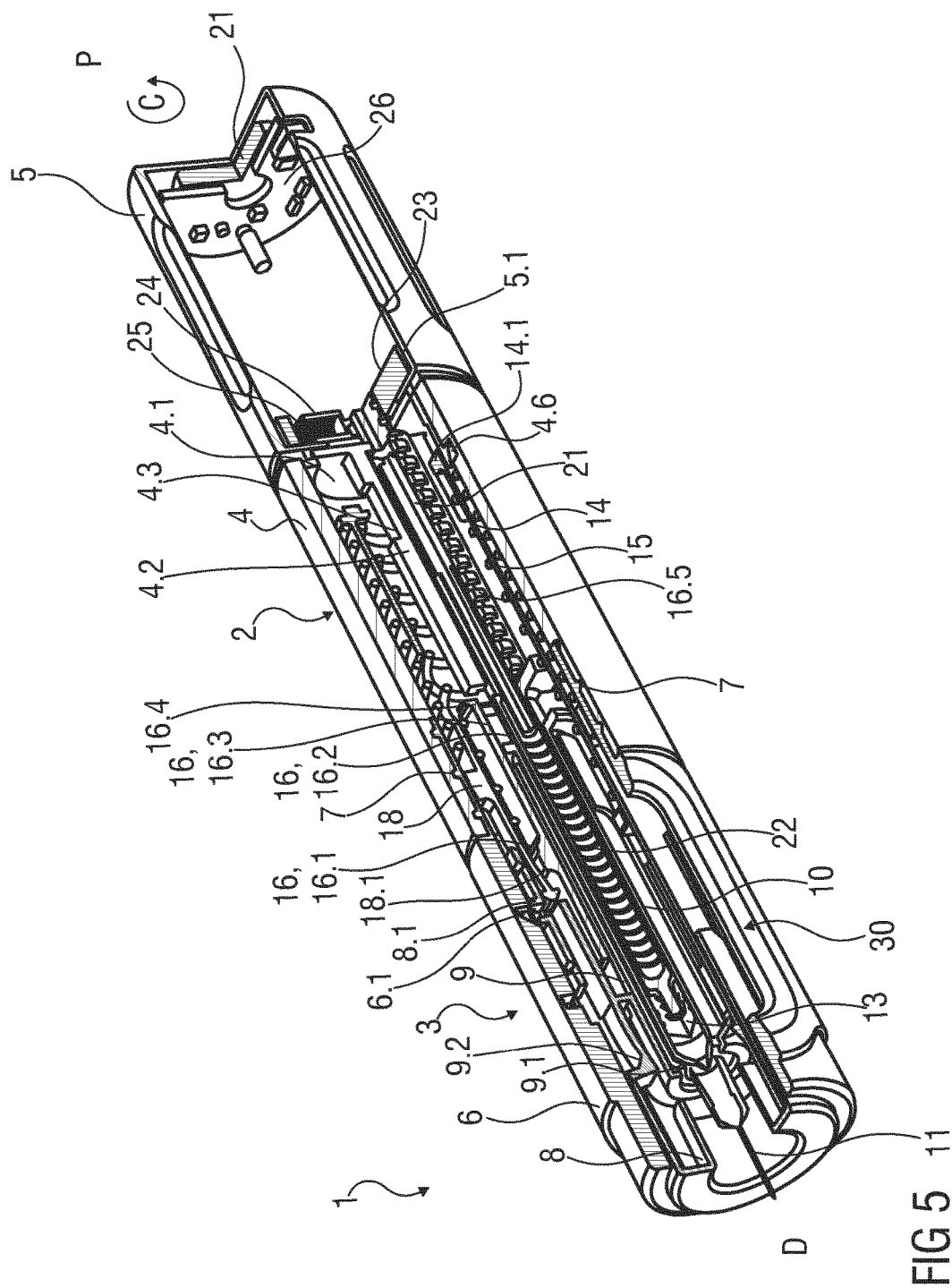
FIG. 5 is a perspective sectional view of the auto-injector with a plunger advanced to dispense a drug.

Immediately prior to the end of injection with the stopper 13 having almost bottomed out in the syringe 10 as illustrated in FIG. 5 the noise rod 21 is released. Hence, the noise rod 21 is accelerated in the proximal direction P and impacts on a stop in the proximal end of the threaded extension 16.5 of the plunger 16 producing audible and tactile feedback to the user that the injection is about finished. The stack up of tolerances, most notably due to the syringe 10 requires that the noise rod 21 must always be released prior to the end of injection. Otherwise, with certain combinations of parts, the noise rod 21 would not always release. The release of the noise rod 21 may be triggered by the piston rod 16.2 interacting with a feature in the bore of the plunger guiding casework 4.2 the rear syringe carrier 14.

Figure 6:
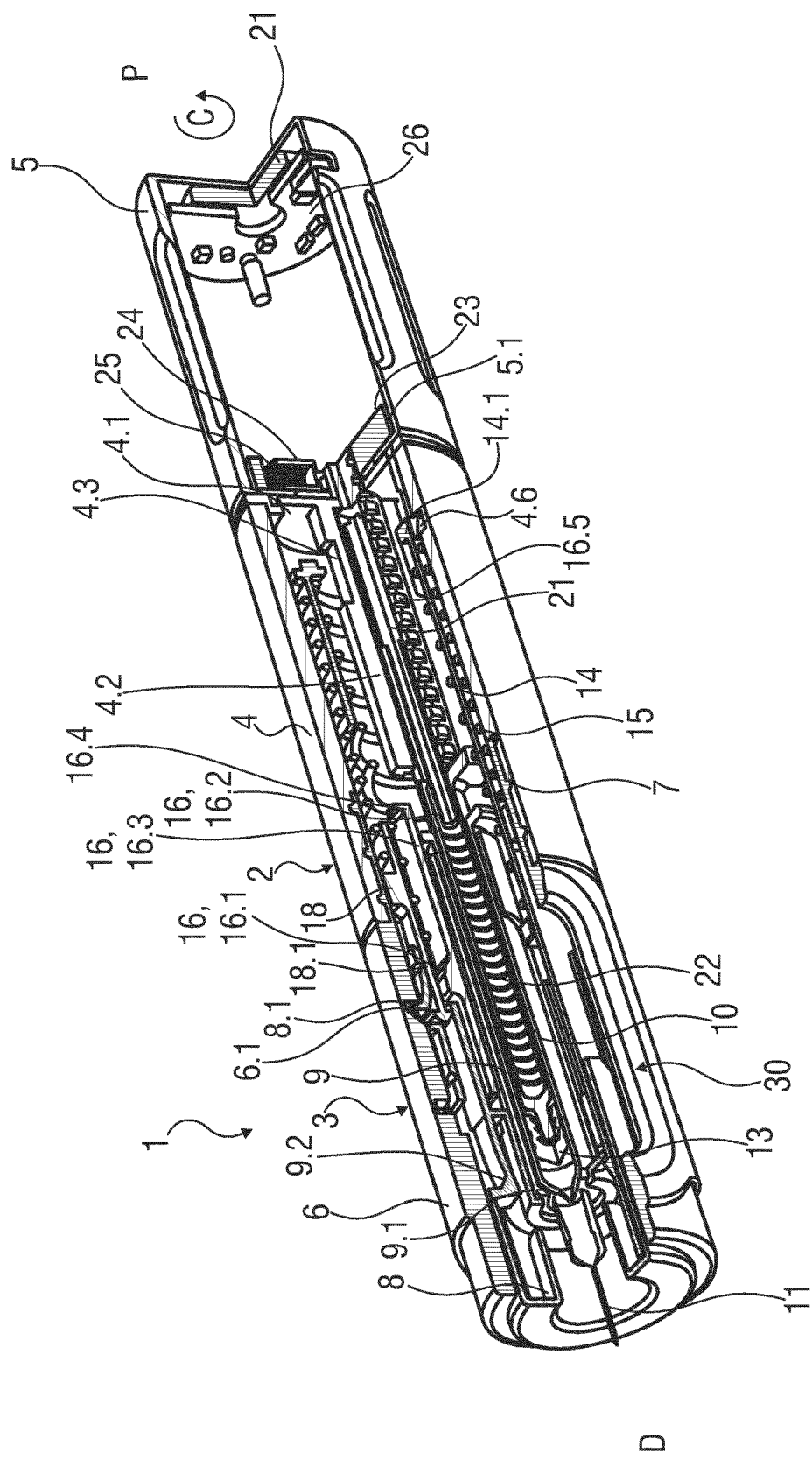
FIG. 6 is a perspective sectional view of the auto-injector at the end of drug delivery.

FIG. 6 shows the auto-injector 1 with the stopper 13 having entirely bottomed out in the syringe 10.

Figure 7:
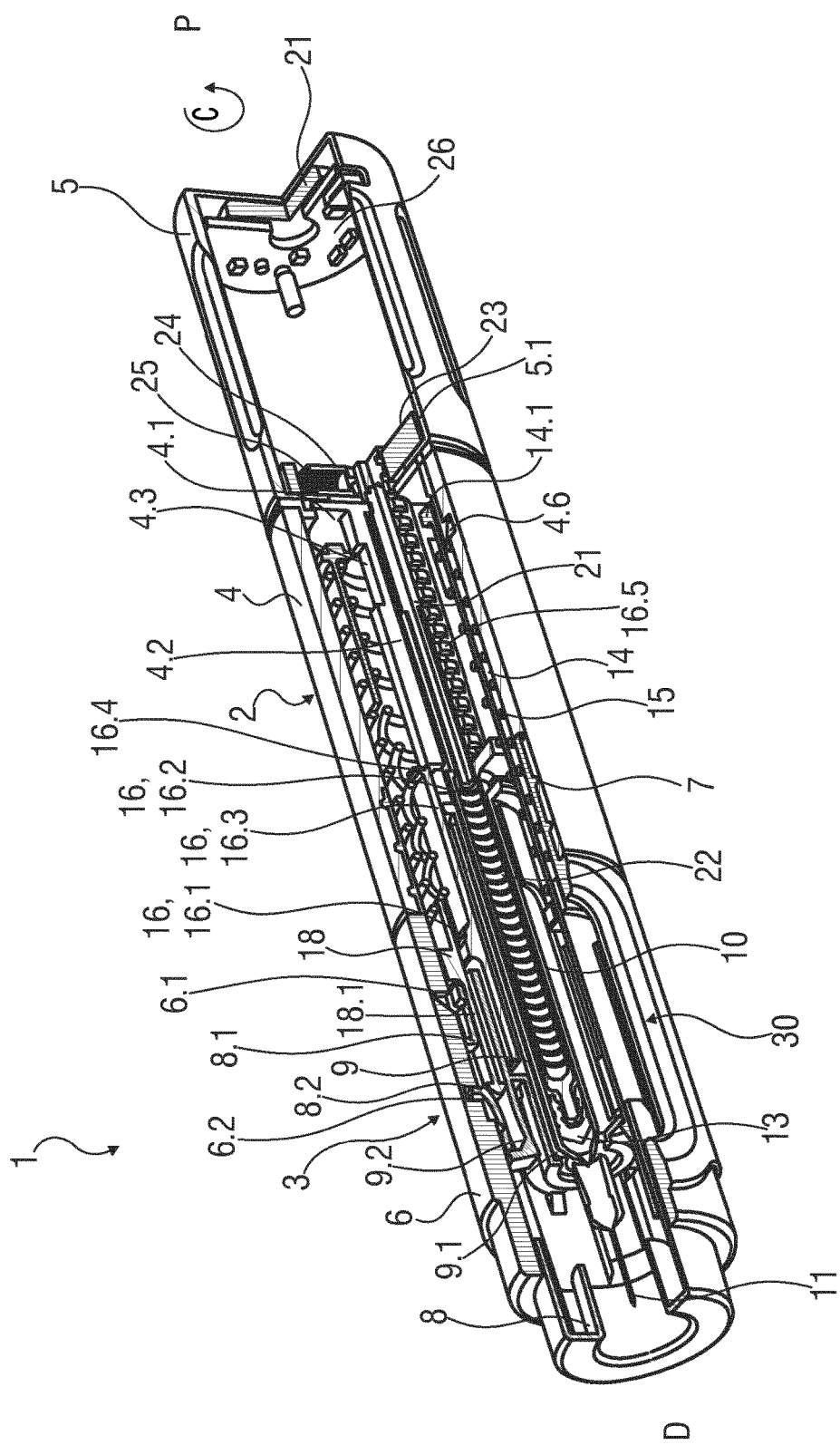
FIG. 7 is a perspective sectional view of the auto-injector after removal from an injection site.

If the user wishes to end the injection, at any time, they must allow the trigger sleeve 8 to move in the distal direction D. FIG. 7 shows the auto-injector 1 lifted from the injection site with the trigger sleeve 8 having moved in the distal direction D so that it protrudes from the distal end of the syringe case 6. This moves a clip 8.1 on the trigger sleeve 8 which had previously been prevented from outward deflection by the syringe case 6 next to a recess 6.1 thus allowing the arrowhead 18.1 to be ramped outwards, disengage the front syringe carrier 9 and engage the trigger sleeve 8 again. The distal end of the control spring 17 is now grounded in the trigger sleeve 8 and as the trigger sleeve 8 reaches its full extension relative to the syringe case 6 in FIG. 7 the distal end of the control spring 17 is grounded in the syringe case 6 through another clip 8.2 on the trigger sleeve 8 radially outwardly deflected into another recess 6.2 in the syringe case 6 by the arrowhead 18.1. The auto-injector 1 is thus needle safe by the extended trigger sleeve 8 engaged to the syringe case 6.

Figure 8:
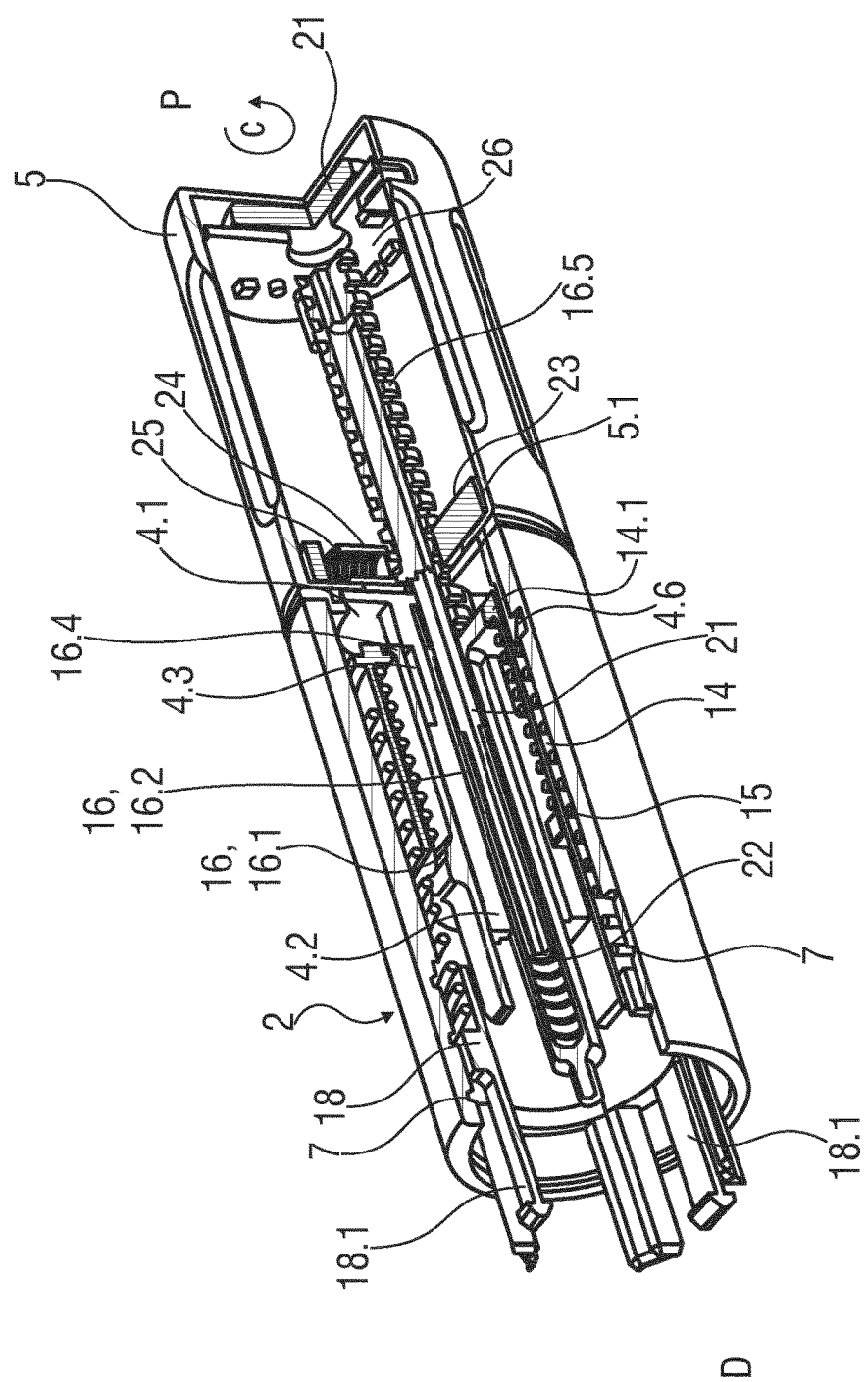
FIG. 8 is a perspective sectional view of a re-usable device of the auto-injector after removal of a packaged syringe.

FIG. 8 is a perspective sectional view of the re-usable device 2 of the auto-injector 1 after removal of the packaged syringe 3. The rear case 5 has been rotated with respect to the front case 4 in a clockwise sense of rotation C thereby retracting the plunger 16 and resetting the drive spring 15. In this position, the compliant plunger arms 16.3 deflect around the proximal end collar 14.1 on the rear syringe carrier 14 relatching the plunger 16 to the rear syringe carrier 14. The rear syringe carrier 14 is restrained from moving in the proximal direction P in this state, e.g. by a latch or friction coupling (not illustrated) to the front case 4. Once the plunger 16 is relatched to the rear syringe carrier 14, the reset procedure continues until the rear syringe carrier 14 and plunger 16 return to the proximal end face 4.1 of the front case 4 as illustrated in FIGS. 1 to 3. The packaged syringe 3 has been unscrewed from the front case 4 and may be safely disposed of. As the needle 11 is retracted within the trigger sleeve 8 the packaged syringe 3 serves as a sharps container. The re-usable device 2 is ready to be connected to a new packaged syringe 3.

Figure 9:
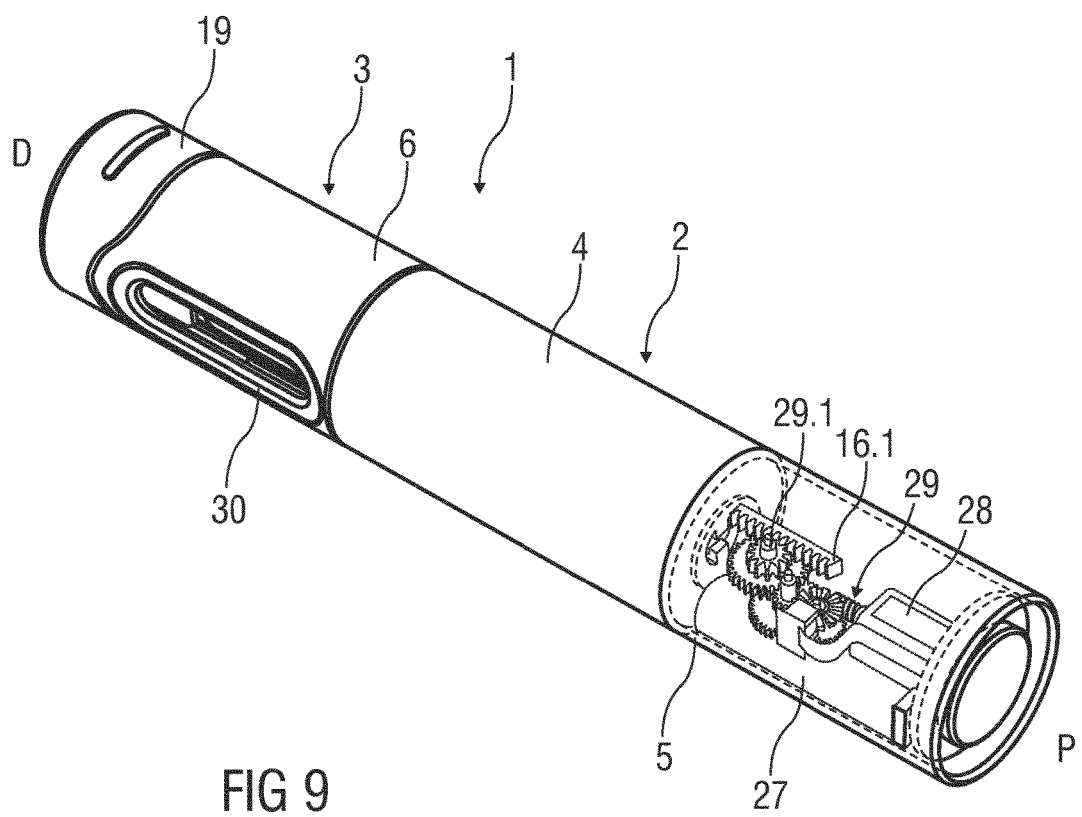
FIG. 9 is a perspective sectional view of an alternative embodiment of the auto-injector.

FIG. 9 is a perspective sectional view of an alternative embodiment of the auto-injector 1. In this embodiment the drive spring is not reset by manually rotating or twisting the rear case 5 relative to the front case 4 but by activating a motor 28 which drives a gear train 29 and retracts the piston rod 16.2 in a rack and pinion manner. The piston rod 16.2 comprises a rack extension 16.6 driven by a gear 29.1. The motor 28 is triggered by the user after removal of the auto-injector 1 from the skin. The motor rotation is converted to a linear motion by the rack and pinion arrangement to pull the plunger 16 back and reset the drive spring 15. When the auto-injector 1 is triggered for starting an injection the rack 16.6 moves in the distal direction D slipping a clutch (not illustrated) in the gear train 29. In this embodiment a second battery 27 may be arranged. An encoder 31 is arranged for determining the position of the plunger 16 in order to assess whether or not it is fully retracted so that the motor 28 can be stopped. The encoder 31 may comprise a slotted wheel and an optoelectronic coupler.

Figure 10:
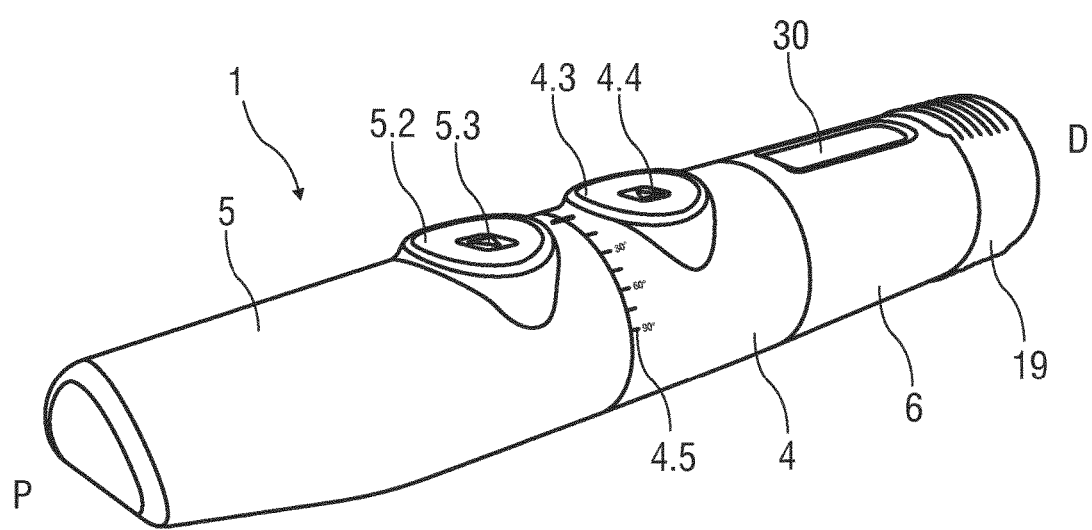
FIG. 10 is a perspective view of an exemplary embodiment of an auto-injector.

FIG. 10 is a perspective view of an exemplary embodiment of the auto-injector 1 with manual reset by twisting or rotating the rear case 5 with respect to the front case 4. The rear case 5 and front case 4 comprise respective thumb rests 4.3, 5.2 with direction symbols 4.4, 5.3 indicating the sense of rotation for resetting the drive spring 15. The front case 4 comprises a graduated scale 4.5 for indicating correct assembly of the front case 4 and rear case 5.

The auto-injector 1 is needle safe at all times for the following reasons: When a new packaged syringe 3 is connected to the reusable device 2 the needle 11 is protected by the needle boot 12 and the protective cap 19. The needle boot 12 is removed with the protective cap 19 while the needle tip remains fully retracted within the syringe case 6 until injection. The needle 11 penetrates the skin only while the auto-injector 1 is in contact with the skin. If the auto-injector 1 loses contact with the skin or on completion of the injection process then the trigger sleeve 8 automatically advances and locks down over the needle 11. As the used packaged syringe 3 is unscrewed and removed from the reusable device 2 the packaged syringe 3 can not be opened or deployed again as the trigger sleeve 8 locks in the extended position and cannot be depressed again. These features may reduce the chance of the user incurring an injury when using the auto-injector 1.

The auto-injector 1 may be arranged to detect an attempt to operate the auto-injector 1 with a previously used, emptied or partially empty packaged syringe 3. This may help prevent injury to the user.

The auto-injector 1 may be arranged for wireless and/or wired communications with external data processing devices, such as a database from a healthcare provider, a home monitoring device or a central home hub for connection to a stakeholder. This connectivity may improve compliance at home by recording time, date, drug, and patient for every injection taken.

Communication with the healthcare provider may involve a connection to a supply chain, e.g. allowing for automatic reordering of the next treatment, authentication of the user, submission of product recalls from the healthcare provider to the user, pay as you go orders, interface for clinicians, e.g. for remote review of a patient condition based on in home diagnostics and/or remote adjustment of the treatment schedule, dose and drug.

Furthermore, the connectivity may allow for:
notification of emergency conditions detected by diagnostics
remote authorisation of additional doses or drugs
interface for the user's family
remote review of patient condition
compliance monitoring/reassurance that patient is taking their medication
interface for patient
remote review of treatment schedule and diagnostics summary
forum to feedback how the patient feels It goes without saying that all senses of rotation mentioned in the above embodiments are chosen by way of example only. The senses of rotation could also be opposite to the ones described, e.g. for providing different versions for right-handed and left-handed users.

The term "drug" or "medicament", as used herein, means a pharmaceutical formulation containing at least one pharmaceutically active compound, wherein in one embodiment the pharmaceutically active compound has a molecular weight up to 1500 Da and/or is a peptide, a proteine, a polysaccharide, a vaccine, a DNA, a RNA, an enzyme, an antibody or a fragment thereof, a hormone or an oligonucleotide, or a mixture of the above-mentioned pharmaceutically active compound, wherein in a further embodiment the pharmaceutically active compound is useful for the treatment and/or prophylaxis of diabetes mellitus or complications associated with diabetes mellitus such as diabetic retinopathy, thromboembolism disorders such as deep vein or pulmonary thromboembolism, acute coronary syndrome (ACS), angina, myocardial infarction, cancer, macular degeneration, inflammation, hay fever, atherosclerosis and/or rheumatoid arthritis, wherein in a further embodiment the pharmaceutically active compound comprises at least one peptide for the treatment and/or prophylaxis of diabetes mellitus or complications associated with diabetes mellitus such as diabetic retinopathy, wherein in a further embodiment the pharmaceutically active compound comprises at least one human insulin or a human insulin analogue or derivative, glucagon-like peptide (GLP-1) or an analogue or derivative thereof, or exendin-3 or exendin-4 or an analogue or derivative of exendin-3 or exendin-4.

Insulin analogues are for example Gly(A21), Arg(B31), Arg(B32) human insulin; Lys(B3), Glu(B29) human insulin; Lys(B28), Pro(B29) human insulin; Asp(B28) human insulin; human insulin, wherein proline in position B28 is replaced by Asp, Lys, Leu, Val or Ala and wherein in position B29 Lys may be replaced by Pro; Ala(B26) human insulin; Des(B28-B30) human insulin; Des(B27) human insulin and Des(B30) human insulin.

Insulin derivates are for example B29-N-myristoyl-des(B30) human insulin; B29-N-palmitoyl-des(B30) human insulin; B29-N-myristoyl human insulin; B29-N-palmitoyl human insulin; B28-N-myristoyl LysB28ProB29 human insulin; B28-N-palmitoyl-LysB28ProB29 human insulin; B30-N-myristoyl-ThrB29LysB30 human insulin; B30-N-palmitoyl-ThrB29LysB30 human insulin; B29-N—(N-palmitoyl-Y-glutamyl)-des(B30) human insulin; B29-N—(N-lithocholyl-Y-glutamyl)-des(B30) human insulin; B29-N-(ω-carboxyheptadecanoyl)-des(B30) human insulin and B29-N-(ω-carboxyheptadecanoyl) human insulin.

Exendin-4 for example means Exendin-4(1-39), a peptide of the sequence H-His-Gly-Glu-Gly-Thr-Phe-Thr-Ser-Asp-Leu-Ser-Lys-Gln-Met-Glu-Glu-Glu-Ala-Val-Arg-Leu-Phe-Ile-Glu-Trp-Leu-Lys-Asn-Gly-Gly-Pro-Ser- Ser-Gly-Ala-Pro-Pro-Pro-Ser-NH2.

Exendin-4 derivatives are for example selected from the following list of compounds:
H-(Lys)4-des Pro36, des Pro37 Exendin-4(1-39)-NH2,
H-(Lys)5-des Pro36, des Pro37 Exendin-4(1-39)-NH2,
des Pro36 Exendin-4(1-39),
des Pro36 [Asp28] Exendin-4(1-39),
des Pro36 [IsoAsp28] Exendin-4(1-39),
des Pro36 [Met(O)14, Asp28] Exendin-4(1-39),
des Pro36 [Met(O)14, IsoAsp28] Exendin-4(1-39),
des Pro36 [Trp(O2)25, Asp28] Exendin-4(1-39),
des Pro36 [Trp(O2)25, IsoAsp28] Exendin-4(1-39),
des Pro36 [Met(O)14 Trp(O2)25, Asp28] Exendin-4(1-39),
des Pro36 [Met(O)14 Trp(O2)25, IsoAsp28] Exendin-4(1-39); or
des Pro36 [Asp28] Exendin-4(1-39),
des Pro36 [IsoAsp28] Exendin-4(1-39),
des Pro36 [Met(O)14, Asp28] Exendin-4(1-39),
des Pro36 [Met(O)14, IsoAsp28] Exendin-4(1-39),
des Pro36 [Trp(O2)25, Asp28] Exendin-4(1-39),
des Pro36 [Trp(O2)25, IsoAsp28] Exendin-4(1-39),
des Pro36 [Met(O)14 Trp(O2)25, Asp28] Exendin-4(1-39),
des Pro36 [Met(O)14 Trp(O2)25, IsoAsp28] Exendin-4(1-39),
wherein the group -Lys6-NH2 may be bound to the C-terminus of the Exendin-4 derivative;
or an Exendin-4 derivative of the sequence des Pro36 Exendin-4(1-39)-Lys6-NH2 (AVE0010),
H-(Lys)6-des Pro36 [Asp28] Exendin-4(1-39)-Lys6-NH2,
des Asp28 Pro36, Pro37, Pro38Exendin-4(1-39)-NH2,
H-(Lys)6-des Pro36, Pro38 [Asp28] Exendin-4(1-39)-NH2, H-Asn-(Glu)5des Pro36, Pro37, Pro38 [Asp28] Exendin-4 (1-39)-NH2,
des Pro36, Pro37, Pro38 [Asp28] Exendin-4(1-39)-(Lys)6-NH2,
H-(Lys)6-des Pro36, Pro37, Pro38 [Asp28] Exendin-4(1-39)-(Lys)6-NH2,
H-Asn-(Glu)5-des Pro36, Pro37, Pro38 [Asp28] Exendin-4(1-39)-(Lys)6-NH2,
H-(Lys)6-des Pro36 [Trp(O2)25, Asp28] Exendin-4(1-39)-Lys6-NH2,
H-des Asp28 Pro36, Pro37, Pro38 [Trp(O2)25] Exendin-4(1-39)-NH2,
H-(Lys)6-des Pro36, Pro37, Pro38 [Trp(O2)25, Asp28] Exendin-4(1-39)-NH2,
H-Asn-(Glu)5-des Pro36, Pro37, Pro38 [Trp(O2)25, Asp28] Exendin-4(1-39)-NH2,
des Pro36, Pro37, Pro38 [Trp(O2)25, Asp28] Exendin-4(1-39)-(Lys)6-NH2,
H-(Lys)6-des Pro36, Pro37, Pro38 [Trp(O2)25, Asp28] Exendin-4(1-39)-(Lys)6-NH2,
H-Asn-(Glu)5-des Pro36, Pro37, Pro38 [Trp(O2)25, Asp28] Exendin-4(1-39)-(Lys)6-NH2,
H-(Lys)6-des Pro36 [Met(O)14, Asp28] Exendin-4(1-39)-Lys6-NH2,
des Met(O)14 Asp28 Pro36, Pro37, Pro38 Exendin-4(1-39)-NH2,
H-(Lys)6-desPro36, Pro37, Pro38 [Met(O)14, Asp28] Exendin-4(1-39)-NH2,
H-Asn-(Glu)5-des Pro36, Pro37, Pro38 [Met(O)14, Asp28] Exendin-4(1-39)-NH2,
des Pro36, Pro37, Pro38 [Met(O)14, Asp28] Exendin-4(1-39)-(Lys)6-NH2,
H-(Lys)6-des Pro36, Pro37, Pro38 [Met(O)14, Asp28] Exendin-4(1-39)-(Lys)6-NH2,
H-Asn-(Glu)5 des Pro36, Pro37, Pro38 [Met(O)14, Asp28] Exendin-4(1-39)-(Lys)6-NH2,
H-Lys6-des Pro36 [Met(O)14, Trp(O2)25, Asp28] Exendin-4(1-39)-Lys6-NH2,
H-des Asp28 Pro36, Pro37, Pro38 [Met(O)14, Trp(O2)25] Exendin-4(1-39)-NH2,
H-(Lys)6-des Pro36, Pro37, Pro38 [Met(O)14, Asp28] Exendin-4(1-39)-NH2,
H-Asn-(Glu)5-des Pro36, Pro37, Pro38 [Met(O)14, Trp(O2)25, Asp28] Exendin-4(1-39)-NH2,
des Pro36, Pro37, Pro38 [Met(O)14, Trp(O2)25, Asp28] Exendin-4(1-39)-(Lys)6-NH2,
H-(Lys)6-des Pro36, Pro37, Pro38 [Met(O)14, Trp(O2)25, Asp28] Exendin-4(S1-39)-(Lys)6-NH2,
H-Asn-(Glu)5-des Pro36, Pro37, Pro38 [Met(O)14, Trp(O2)25, Asp28] Exendin-4(1-39)-(Lys)6-NH2;
or a pharmaceutically acceptable salt or solvate of any one of the afore-mentioned Exendin-4 derivative.

Hormones are for example hypophysis hormones or hypothalamus hormones or regulatory active peptides and their antagonists as listed in Rote Liste, ed. 2008, Chapter 50, such as Gonadotropine (Follitropin, Lutropin, Choriongonadotropin, Menotropin), Somatropine (Somatropin), Desmopressin, Terlipressin, Gonadorelin, Triptorelin, Leuprorelin, Buserelin, Nafarelin, Goserelin.

A polysaccharide is for example a glucosaminoglycane, a hyaluronic acid, a heparin, a low molecular weight heparin or an ultra low molecular weight heparin or a derivative thereof, or a sulphated, e.g. a poly-sulphated form of the above-mentioned polysaccharides, and/or a pharmaceutically acceptable salt thereof. An example of a pharmaceutically acceptable salt of a poly-sulphated low molecular weight heparin is enoxaparin sodium.

Antibodies are globular plasma proteins (~150 kDa) that are also known as immunoglobulins which share a basic structure. As they have sugar chains added to amino acid residues, they are glycoproteins. The basic functional unit of each antibody is an immunoglobulin (Ig) monomer (containing only one Ig unit); secreted antibodies can also be dimeric with two Ig units as with IgA, tetrameric with four Ig units like teleost fish IgM, or pentameric with five Ig units, like mammalian IgM.

The Ig monomer is a "Y"-shaped molecule that consists of four polypeptide chains; two identical heavy chains and two identical light chains connected by disulfide bonds between cysteine residues. Each heavy chain is about 440 amino acids long; each light chain is about 220 amino acids long. Heavy and light chains each contain intrachain disulfide bonds which stabilize their folding. Each chain is composed of structural domains called Ig domains. These domains contain about 70-110 amino acids and are classified into different categories (for example, variable or V, and constant or C) according to their size and function. They have a characteristic immunoglobulin fold in which two β sheets create a "sandwich" shape, held together by interactions between conserved cysteines and other charged amino acids.

There are five types of mammalian Ig heavy chain denoted by α, δ, ε, γ, and μ. The type of heavy chain present defines the isotype of antibody; these chains are found in IgA, IgD, IgE, IgG, and IgM antibodies, respectively.

Distinct heavy chains differ in size and composition; α and γ contain approximately 450 amino acids and δ approximately 500 amino acids, while μ and ε have approximately 550 amino acids. Each heavy chain has two regions, the constant region ($C_H$) and the variable region ($V_H$). In one species, the constant region is essentially identical in all antibodies of the same isotype, but differs in antibodies of different isotypes. Heavy chains γ, α and δ have a constant region composed of three tandem Ig domains, and a hinge region for added flexibility; heavy chains μ and ε have a constant region composed of four immunoglobulin domains. The variable region of the heavy chain differs in antibodies produced by different B cells, but is the same for all antibodies produced by a single B cell or B cell clone. The variable region of each heavy chain is approximately 110 amino acids long and is composed of a single Ig domain.

In mammals, there are two types of immunoglobulin light chain denoted by λ and κ. A light chain has two successive domains: one constant domain (CL) and one variable domain (VL). The approximate length of a light chain is 211 to 217 amino acids. Each antibody contains two light chains that are always identical; only one type of light chain, κ or λ, is present per antibody in mammals.

Although the general structure of all antibodies is very similar, the unique property of a given antibody is determined by the variable (V) regions, as detailed above. More specifically, variable loops, three each the light (VL) and three on the heavy (VH) chain, are responsible for binding to the antigen, i.e. for its antigen specificity. These loops are referred to as the Complementarity Determining Regions (CDRs). Because CDRs from both VH and VL domains contribute to the antigen-binding site, it is the combination of the heavy and the light chains, and not either alone, that determines the final antigen specificity.

An "antibody fragment" contains at least one antigen binding fragment as defined above, and exhibits essentially the same function and specificity as the complete antibody of which the fragment is derived from. Limited proteolytic digestion with papain cleaves the Ig prototype into three fragments. Two identical amino terminal fragments, each containing one entire L chain and about half an H chain, are the antigen binding fragments (Fab). The third fragment, similar in size but containing the carboxyl terminal half of both heavy chains with their interchain disulfide bond, is the crystalizable fragment (Fc). The Fc contains carbohydrates, complement-binding, and FcR-binding sites. Limited pepsin digestion yields a single F(ab')2 fragment containing both Fab pieces and the hinge region, including the H—H interchain disulfide bond. F(ab')2 is divalent for antigen binding. The disulfide bond of F(ab')2 may be cleaved in order to obtain Fab'. Moreover, the variable regions of the heavy and light chains can be fused together to form a single chain variable fragment (scFv).

Pharmaceutically acceptable salts are for example acid addition salts and basic salts. Acid addition salts are e.g. HCl or HBr salts. Basic salts are e.g. salts having a cation selected from alkali or alkaline, e.g. Na+, or K+, or Ca2+, or an ammonium ion N+(R1)(R2)(R3)(R4), wherein R1 to R4 independently of each other mean: hydrogen, an optionally substituted C1-C6-alkyl group, an optionally substituted C2-C6-alkenyl group, an optionally substituted C6-C10-aryl group, or an optionally substituted C6-C10-heteroaryl group. Further examples of pharmaceutically acceptable salts are described in "Remington's Pharmaceutical Sciences" 17. ed. Alfonso R. Gennaro (Ed.), Mark Publishing Company, Easton, Pa., U.S.A., 1985 and in Encyclopedia of Pharmaceutical Technology.

Pharmaceutically acceptable solvates are for example hydrates.

Those of skill in the art will understand that modifications (additions and/or removals) of various components of the apparatuses, methods and/or systems and embodiments described herein may be made without departing from the full scope and spirit of the present invention, which encompass such modifications and any and all equivalents thereof.

needle, wherein a barb is attached in the inner sleeve engageable to the protective needle boot for joint axial translation;

a case configured to receive the syringe, the case comprising a front case rotatably coupled to a rear case, a drive spring arranged to advance a plunger relative to the syringe during an injection, and a reset mechanism configured to convert rotation of the rear case relative to the front case in a first sense of rotation into linear motion of the plunger to retract the plunger from an end-of-injection position and compress the drive spring.

2. The auto-injector according to claim 1, wherein the plunger comprises a threaded extension and wherein the rear case comprises a screw nut configured to releasably engage the threaded extension such that the plunger is retractable by rotation of the rear case relative to the front case.

3. The auto-injector of claim 2, wherein the screw nut is arranged as a ratchet wheel coupled to at least one ratchet drive feature in the rear case such that the ratchet wheel is rotatably coupled to the rear case in the first sense of rotation and the ratchet wheel rotates relative to the rear case in a second sense of rotation opposite to the first sense of rotation.

4. The auto-injector of claim 2, comprising a release clip arranged in the screw nut and configured to be biased to engage the threaded extension.

5. The auto-injector of claim 4, wherein the release clip is configured to release the threaded extension when the trigger sleeve is translated in a proximal direction relative to the case.

6. The auto-injector of claim 2, wherein the rear case and front case each comprises a thumb rest comprising a direction symbol indicating the first sense of rotation.

The invention claimed is:

1. An auto-injector for administering a medicament, comprising:

a syringe comprising an injection needle and a syringe case, wherein a protective cap is arrangeable on the syringe case, the cap having an inner sleeve arrangeable inside a trigger sleeve of the syringe and over a protective needle boot for protecting the injection 7. The auto-injector of claim 1, further comprising a syringe carrier configured to retain the syringe and a control spring arranged to advance the syringe carrier relative to the case for needle insertion.

8. The auto-injector of claim 7, wherein the plunger is coupled to the syringe carrier when retracted, and the plunger is released from the syringe carrier when the syringe carrier is advanced to a predetermined position relative to the case.

9. The auto-injector of claim 7, wherein the control spring distally bears against a control collar operatively coupled to the syringe carrier or the trigger sleeve depending at least on a position of the trigger sleeve relative to the case.

10. The auto-injector of claim 1, wherein a releasable noise rod is provided, capable of, upon release, generating at least one of an audible feedback and a tactile feedback to a user, wherein the noise rod is configured to be released when the plunger reaches a position relative to the syringe in which a stopper is located in proximity of a distal end of the syringe.

11. The auto-injector of claim 1, wherein a control unit is configured to:
store time stamped user operations, and
exchange data with an external data base.

12. The apparatus of claim 1, wherein the front case is arranged distally from the rear case.

13. The apparatus of claim 1, wherein the front case receives the syringe.

14. An auto-injector for administering a medicament, comprising:
a syringe comprising an injection needle;
a case configured to receive the syringe, the case comprising a front case rotatably coupled to a rear case;
a syringe carrier configured to retain the syringe and a control spring arranged to advance the syringe carrier relative to the case for needle insertion;
a drive spring arranged to advance a plunger relative to the syringe during an injection; and
a reset mechanism configured to convert rotation of the rear case relative to the front case in a first sense of rotation into linear motion of the plunger to retract the plunger from an end-of-injection position and compress the drive spring;
wherein the plunger is coupled to the syringe carrier when retracted, and the plunger is released from the syringe carrier when the syringe carrier is advanced to a predetermined position relative to the case.

15. An auto-injector for administering a medicament, comprising:
a syringe comprising an injection needle;
a case configured to receive the syringe, the case comprising a front case rotatably coupled to a rear case;
a drive spring arranged to advance a plunger relative to the syringe during an injection; and
a reset mechanism configured to convert rotation of the rear case relative to the front case in a first sense of rotation into linear motion of the plunger to retract the plunger from an end-of-injection position and compress the drive spring;
wherein the plunger comprises a threaded extension and the rear case comprises a screw nut configured to releasably engage the threaded extension such that the plunger is retractable by rotation of the rear case relative to the front case; and
wherein the screw nut is arranged as a ratchet wheel coupled to at least one ratchet drive feature in the rear case such that the ratchet wheel is rotatably coupled to the rear case in the first sense of rotation and the ratchet wheel rotates relative to the rear case in a second sense of rotation opposite to the first sense of rotation.

* * * * *

UNITED STATES PATENT AND TRADEMARK OFFICE
CERTIFICATE OF CORRECTION

PATENT NO. : 10,384,007 B2
APPLICATION NO. : 14/435563
DATED : August 20, 2019
INVENTOR(S) : Charley Henderson et al.

Page 1 of 1

It is certified that error appears in the above-identified patent and that said Letters Patent is hereby corrected as shown below:

In the Claims

Column 15, Line 16, Claim 12, delete "apparatus" and insert -- auto-injector --

Column 15, Line 18, Claim 13, delete "apparatus" and insert -- auto-injector --

Signed and Sealed this
Seventh Day of January, 2020

Andrei Iancu
*Director of the United States Patent and Trademark Office*